United States Patent [19]

Meinert

[11] Patent Number: 5,563,306
[45] Date of Patent: Oct. 8, 1996

[54] METHOD OF PURIFYING PERFLUOROCARBONS, AND USE OF THE PERFLUOROCARBONS THUS PURIFIED

[75] Inventor: Hasso Meinert, Neu-Ulm, Germany

[73] Assignee: Pharmpur GmbH, Augsburg, Germany

[21] Appl. No.: 290,833

[22] PCT Filed: Jan. 21, 1993

[86] PCT No.: PCT/DE93/00061

§ 371 Date: Nov. 3, 1994

§ 102(e) Date: Nov. 3, 1994

[87] PCT Pub. No.: WO93/16974

PCT Pub. Date: Sep. 2, 1993

[30] Foreign Application Priority Data

Feb. 21, 1992 [DE] Germany .......................... 42 05 341.2

[51] Int. Cl.$^6$ .......................... C07C 17/38; C07C 17/395; C07C 19/08; C07C 23/36
[52] U.S. Cl. .......................... 570/177; 564/497; 570/178
[58] Field of Search .................... 570/177, 178; 564/497

[56] References Cited

U.S. PATENT DOCUMENTS

| 2,691,052 | 10/1954 | Cines | 570/177 |
| 2,738,371 | 3/1956 | Parmelee | 570/177 |
| 4,766,261 | 8/1988 | Bierl | 570/178 |
| 5,352,785 | 10/1994 | Herzberg et al. | 564/497 |

*Primary Examiner*—Joseph E. Evans
*Attorney, Agent, or Firm*—Keck, Mahin & Cate

[57] ABSTRACT

Described is a method for the purification of perfluorocarbons, or mixtures of perfluorocarbons, having impurities containing hydrogen and/or carbon-carbon double bonds. The impure perfluorocarbons or perfluorocarbon mixtures are reacted with strong aqueous bases in the presence of $Ca^{2+}$ or $Ba^{2+}$ ions and alcoholate ions together with secondary amines.

14 Claims, No Drawings

METHOD OF PURIFYING PERFLUOROCARBONS, AND USE OF THE PERFLUOROCARBONS THUS PURIFIED

DESCRIPTION

The invention pertains to a process for purification of perfluorocarbons or perfluorocarbon mixtures with impurities containing hydrogen and/or carbon-carbon double bonds.

Perfluorocarbons prepared in a known manner, e.g., via electrofluorination or by a $CoF_3$ process or by direct fluorination, contain varying amounts of partially fluorinated substances depending on the preparation process, i.e., compounds that still contain hydrogen and/or carbon-carbon multiple bonds in the molecule. These by-products have increased chemical reactivity and toxicity compared to the perfluorinated compounds. For most areas of application, especially in the areas of medicine and microelectronics, it is indispensable to remove these compounds.

For this, the processes described to date utilize the higher, compared to perfluorocarbons, chemical reactivity regarding nucleophiles such as alkalis, amines, and oxidizing agents.

Thus, according to JP 60-112,724, treatment with a very highly concentrated solution is proposed. C. Fukaya et al. (10th Int. Symp. Fluorine Chem., Vancouver, August 1–6, 1982) do a combined treatment with isobutylamine and potassium hydroxide which is followed by an acid rinse. According to U.S. Pat. No. 4,328,376, ammonia or primary or secondary amines are used for purification of perfluorinated ethers.

In the above-indicated processes, the products to be purified are boiled with reflux for several days at normal pressure. Le Blanc et al. (Nouveau J. Chim. 8 (1984) 251) describe purification by shaking with 10% aqueous KOH and subsequent filtration over activated carbon and aluminum oxide. Weeks (U.S. Pat. No. 3,696,156) also does the purification with sodium hydroxide on $Al_2O_3$.

Conte et al. (Chimicaoggi 11 (1988) 61) describe a purification process for perfluoro-N,N-diethylcyclohexylamine by means of diethylamine in an autoclave at 120° C., rinsing of the reaction products with water, and subsequent autoclaving with 10% alcoholic KOH solution at 120° C. and 5 atm.

A treatment with a mixture of CaO, NaOH, and water by Huang et al. (J. Fluorine Chem. 45 (1989) 239) is done not as a purification process but as a process for chemical decomposition of H-containing fluorine compounds. This reaction is based on a publication of Wallin et al. (Anesthesia and Analgesia 54 (1975) 758) on the stability of a fluorinated ether as anesthetic.

For analytical determination of the eliminatable HF and thus the fluorine ion from compounds with $-CF_2CHF$ groups, Meinert et al. (Forschungsbericht, AdW [Akademie der Wissenschaften], Berlin 1986) use a reaction with hexamethylenediamine at 120° C. This reaction was later done in a homogeneous phase by Gross et al. (Mittbl. Chem. Ges. 37 (1990) 1461) in the presence of nonane.

According to Radeck et al. (DD 287,478), the perfluorocarbons to be purified are treated with high-valance metal fluorides at temperatures of 350°–500° C. over a period of 0.5–6 h.

Meinert et al. (1989 Intern. Chem. Congr. Pacific Basin Soc., Honolulu, No. 174; Final report BMFT Project "PFC Emulsions" 1988; J. Fluorine Chem. 51 (1991) 53) used a pressure purification wherein the raw product is autoclaved with concentrated KOH, secondary amine, and CaO at 170°–200° C.

Some authors also propose extractive processes for purification of perfluorocarbons; thus, e.g., in U.S. Pat. No. 3,887,629, a liquid-liquid extraction with hydrocarbons, or in U.S. Pat. No. 3,449,218, an azeotropic distillation of perfluorocarbons with oxygen-containing hydrocarbons such as acetone. However, the degree of purity of the perfluorocarbons that can be attained with this is not yet adequate for biological and medicinal purposes so that it can only be considered a preliminary purification.

It is the object of the invention to make available a simple, highly effective process for elimination of compounds containing hydrogen and/or double bonds from perfluorocarbons or other mixtures.

This object is attained according to the invention by reacting the perfluorocarbons or perfluorocarbon mixtures to be purified with nucleophilic reagents, especially a secondary amine, $R_2NH$, and/or alcoholate ions and a strong base, especially KOH or NaOH in the presence of $Ca^{2+}$ or $Ba^{2+}$ ions. In this manner, highly pure perfluorocarbons are obtained which are absolutely free of hydrogen atoms that are possibly still bonded or fluoroolefinic double bonds and thus can be used directly in medicine, biology, and electronics.

The thus-purified perfluorocarbons or perfluorocarbon mixtures are chemically inert biocompatible compounds, gases, or usually liquids, which can be used in medicine, biology, and microelectronics due to their properties.

The perfluorocarbons or perfluorocarbon mixtures to be purified are essentially substances or mixtures of substances whose molecules consist of a carbon skeleton in which one or several carbon atoms are replaced by a hetero atom such as nitrogen and/or oxygen and/or sulfur and/or phosphorus atoms and in which there are only single bonds between the carbon atoms or between the carbon and hetero atoms, and all additional conditions bonds are saturated with fluorine atoms.

They can be prepared from the corresponding CH analogous starting compounds, especially by electrochemical fluorination, but also by other fluorination processes.

Depending on the method of preparation, these products can contain compounds as impurities that still contain hydrogen atoms or carbon-carbon double bonds and which can be identical in their basic structure to the perfluorinated compounds.

The invention creates a purification process that is superior in effectiveness and operation to the present state of the art.

Liquid perfluorocarbons are practically insoluble in water and only slightly soluble in most organic solvents. Perfluorocarbons are only soluble in one another or in halofluorohydrocarbons.

If, in the state of the art, the perfluorocarbons to be purified are reacted with strong bases and amines in aqueous media, this reaction mixture constitutes a system of three phases which are not miscible with one another: perfluorocarbons/base/amine. Although heating with reflux produces greater mixing and thus contact of the reactants with one another, it requires week-long boiling. Upon reaction in an autoclave, the reaction conditions with respect to mixing and reaction time are improved.

However, a reaction of the product to be purified with amines without strong aqueous bases precludes removal of eliminatable HF via neutralization with strong bases in an aqueous medium. Also, if only amines are used as a reaction medium, even in pilot-scale processing, much too large amounts of environmentally polluting amines accumulate.

Reaction processes that proceed via several reaction steps, wherein fluoroolefins initially formed with amines are then separated, rinsed, and subsequently reacted with alcoholates in alcohol solution, are very cumbersome and do not substantially improve the previously indicated purification effects.

Processes of postfluorination with compounds reactive with fluorine, e.g., high-valence metal fluorides at temperatures of 400°–500° C., represents sic a postfluorination process, especially for very incompletely fluorinated compounds. However, at the temperatures indicated, notable splitting of double bonds and decomposition of the starting products already occur which counteract the process of high-grade purification.

The purification process of the invention can be characterized in the direction of all reaction steps being attained in a homogeneous phase due to the fact that the phases which are not miscible or barely miscible within one another are partially and adequately homogenized by use of an effective surfactant. In this, in the strong base, the hydrogen that is still bonded is eliminated as HF. The fluoride ions formed in this are removed from the reaction equilibrium as sparingly soluble $CaF_2$ by means of the CaO or $Ca(OH)_2$ which is used concurrently. Thereafter, nucleophilic addition occurs on the fluoroolefinic double bonds by both alcoholate ($RO^-$), preferably formed from a monofunctional alcohol (ROH with $R=CH_3$, $C_2H_5$, $C_3H_7$, $(CH_3)_2CH$, etc.), used in a strongly alkaline medium, and finally by secondary amine after repeated HF elimination. Preferably all reactants are completely reacted in a uniform phase wherein an aqueous, i.e., differentiating, medium is also involved in keeping with the participation of ionic species in the overall reaction process.

Instead of CaO, BaO or $Ba(OH)_2$ can also be used because sparingly soluble $BaF_2$ is also formed in this, and in the subsequent processing by treatment with dil. sulfuric acid, all $Ba^{2+}$ ions are quantitatively precipitated as $BaSO_4$.

The reactions can be described by the following equations:

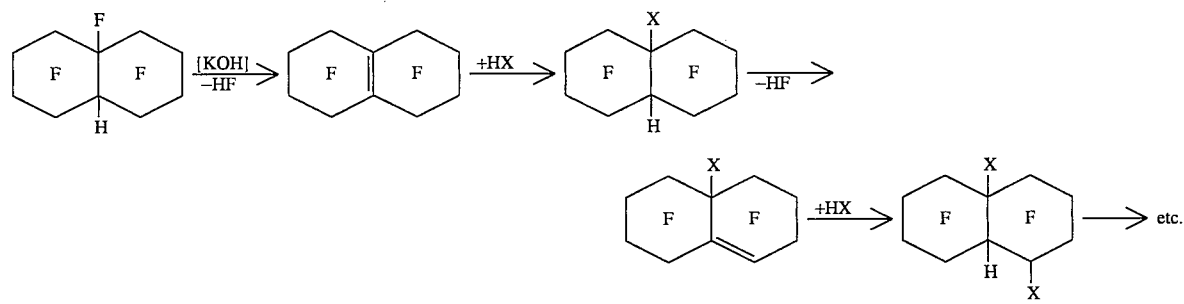

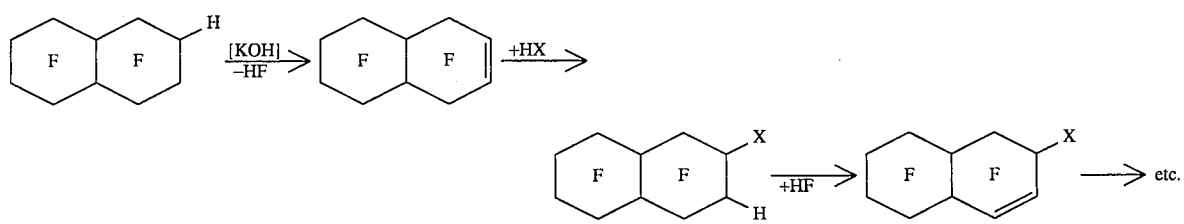

X = RO, $R_2N$

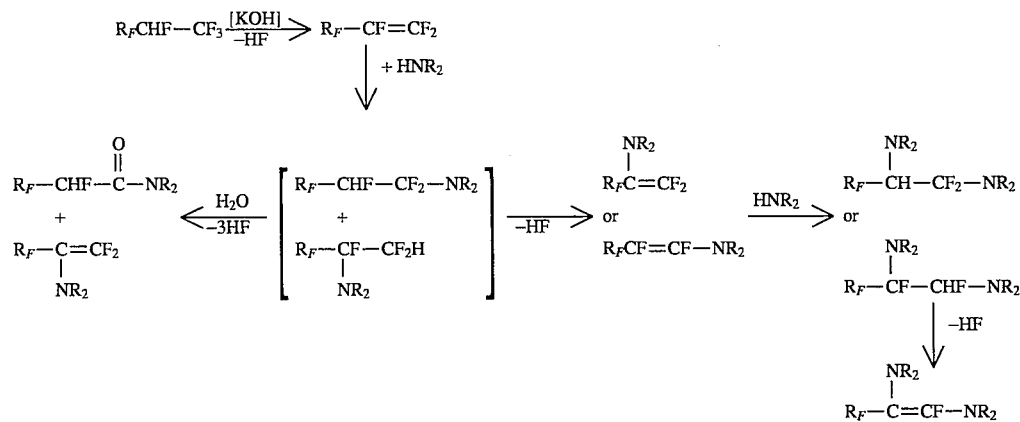

Overall reaction: 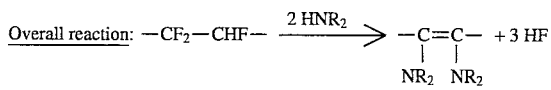

The surfactant to be used can be an ionic or nonionic surfactant. It is stable to bases and amines as well as at the temperatures proposed for the reaction, and it has emulsifying properties for perfluorocarbons. The surfactant concentration need not be greater than 1% (w/v); preferably it is 0.05–0.5% (w/v).

During autoclaving, depending on the products to be used and the elevated temperatures of preferably 150°–200° C., pressures of 5–20 bar arise. In this manner, the formation of a homogeneous phase is especially fostered with the preferred presence of the surfactant.

However, upon boiling of the reaction mixture also, partial and adequate homogenization that fosters the course of the reaction is already attained by additional reflux at normal pressure due to the surfactant effect. Due to the sparing solubility of perfluorocarbons in water, the surfactant should meet the requirements for preparation of perfluorocarbon emulsions (among others, EP 0,231,091; U.S. Pat. Nos. 3,828,085; 4,917,930; CH 665,952; DE 2,224,182 C2; DE 2,555,408 C2; DE 3,326,901 C2; U.S. Pat Nos. 4,325,972; 3,962,439; EP 0,261,802; EP 0,282,948; EP 0,282,949; U.S. Pat. Nos. 3,778,381; 4,865,836; and WO 89/10118), assuming that the surfactant is stable under the proposed process conditions.

For homogenization, preferably surfactants from the group of fluorosurfactants are suited that are stable in a strongly alkaline medium of the type $R_FCOOH$ or $R_FSO_3H$ or their anions, $R_FCOO^-$ or $R_FSO_3^-$ ($R_F=CF_3(CF_2)_n$, n=3–10).

The concentration of the surfactants are maximally 1.0, preferably 0.05–0.5 wt %.

After completion of the purification process, the phases separate of their own accord. In this, the PFC perfluorocarbon phase is reformed with a small proportion of dissolved amine (<1%) as the phase with the greatest specific weight; above this, the aqueous base with dissolved alcoholate/alcohol and surfactant; and above that, the amine.

After removal of solid products, mainly alkaline-earth fluorides, by means of filtration, the liquid phases are separated (e.g., with a separatory funnel). The perfluorocarbon liquid is repeatedly shaken with 2N acid (e.g., sulfuric acid or hydrochloric acid), 1N $NaHCO_3$ solution, as well as with distilled water; is dried on an effective drying agent (e.g., water-free $Na_2SO_4$); and finally fractionally distilled in an effective column.

According to IR, $^1$H-NMR, and GC/MS spectroscopy, the thus-treated perfluorocarbons are free of hydrogen-containing and fluoroolefinic compounds. In contrast to the raw products, the purified perfluorocarbons, as 100% perfluorinated compounds, do not produce inhibition of cell growth according to studies on HeLa or Molt4 or $HEP_2$ cell cultures. The rates of proliferation are determined via DNA synthesis and protein formation.

The highly purified perfluorocarbons of the invention are thus directly usable for medical and biological purposes as well as in microelectronics.

EXAMPLES OF EMBODIMENTS

EXAMPLE 1

1,000 mL of a raw product of perfluorodecalin, which was obtained conventionally by the $CoF_3$ process, are autoclaved with 80 mL diisobutylamine, 80 mL ethanol, 80 mL 8N KOH, 5 g CaO, and 0.5 g perfluorooctanoic acid at 150°–170° C. with stirring at 800 rpm for 72 h.

Thereafter, the reacted product is filtered and the lower phase of the filtrate is removed in a separatory funnel. This phase is rinsed twice with 1,000 mL 2N hydrochloric acid, twice with 1,000 mL $NaHCO_3$ solution, and twice with 1,000 mL distilled water.

Thereafter, it is dried over water-free sodium sulfate, filtered, and fractionally distilled at 141°–142° C. in a cracking column (approximately 100 theoretical plates, reflux ratio 10:1 (10 sec reflux, 1 sec withdrawal)).

No hydrogen-containing compounds or compounds with double bonds can be shown in the purified perfluorodecalin by FT-IR, $^1$H-NMR, or GC/MS spectroscopy.

In comparison and contrast to the raw product, the purified perfluorodecalin shows no proliferation inhibition with respect to DNA and protein synthesis in HeLa or Molt4 or $HEP_2$ cells.

The determination of ionizable fluoride in a reaction of the fluorocarbon with hexamethylenediamine in nonane at 120° C. according to the above-indicated equation for the overall reaction is suitable as a quantitative process for determination of residual CH bonds in fluorocarbons. According to this, no fluoride ions could be shown after the purification process (the limit of detection of the fluoride concentration was $\leq 10^{-5}$ mol.$L^{-1}$).

EXAMPLE 2

2,500 mL of a raw product of perfluorooctane, which was obtained conventionally by the $CoF_3$ process or by direct fluorination, are autoclaved with 100 mL diisobutylamine, 100 mL isopropanol, 200 mL 5N KOH, 15 g BaO, and 1 g perfluorooctanesulfonyl fluoride at 150°–170° C. with stirring (approximately 500 rpm) for 72 h at approximately 10 bar.

Thereafter, the reacted product is filtered and the lower phase of the filtrate is removed in a seperatory funnel. This phase is rinsed twice with 400 mL 2N sulfuric acid, twice with 400 mL saturated $NaHCO_3$ solution, and twice with 400 mL double-distilled water. Thereafter, it is dried over water-free sodium sulfate, filtered, and fractionally distilled at 100.5°–102.5° C. in a cracking column (approximately 100 theoretical plates, reflux ratio 10:1 (10 sec reflux, 1 sec withdrawal)).

In keeping with the analytical and cell toxicology findings given in Example 1, no CH-containing compounds or compounds with double bonds can be shown in the purified perfluorooctane.

EXAMPLE 3

Perfluorotributylamine which was obtained conventionally via electrofluorination of the CH analogous starting product can contain a N—F bond as a result of the-preparation process. For this reason, the raw product is subjected to a preliminary purification by reaction with potassium iodide according to the following:

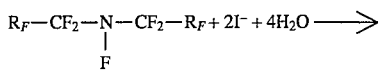

2,500 mL of the prepurified perfluorotributylamine are autoclaved with 100 mL diisobutylamine, 100 mL ethanol, 200 mL 5N KOH, 13 g CaO, and 1 g perfluorooctanoic acid at 150°–170° C. with stirring for 72 h.

The processing of the reacted product occurs as indicated in Examples 1 and 2, wherein it is fractionally distilled at 178°–179.5° C. in a cracking column.

In keeping with the analytical and cell toxicology findings given in Examples 1 and 2, the purified perfluorotributylamine is free of hydrogen-containing compounds or compounds with double bonds. It is also completely free of N—F bonds.

I claim:

1. Process for purification of perfluorocarbons or perfluorocarbon mixtures with hydrogen-containing or carbon-carbon double bond-containing impurities, characterized by the fact that the perfluorocarbons or perfluorocarbon mixtures to be purified are reacted with strong aqueous bases in the presence of $Ca^{2+}$ or $Ba^{2+}$ ions and alcoholate ions as well as secondary amines.

2. Process according to claim 1, characterized by the fact that the perfluorocarbons to be purified are reacted with the reactants in a homogeneous phase.

3. Process according to claim 1, characterized by the fact that a mixture consisting of a perfluorocarbon/aqueous base phase and an alcohol/secondary amine phase is homogenized by means of a surfactant.

4. Process according to claim 1, characterized by the fact that the reaction mixture is autoclaved at temperatures of 150°–200° C.

5. Process according to one of claim 1, characterized by the fact that the reaction mixture is autoclaved at pressures of 5–20 bar.

6. Process according to one of claim 1, characterized by the fact that the reaction mixture is boiled with reflux at normal pressure.

7. Process according one of claim 1, comprising forming the alcoholate ions by the addition of monofunctional alcohol to strong bases which further react as strong nucleophiles with fluoroolefins formed by HF elimination.

8. Process according to claim 7, wherein the monofunctional alcohol is designated ROH in which R is selected from the group consisting of $CH_3$, $C_2H_5$, $C_3H_7$, and $(CH_3)_2CH$.

9. Process according to one of claim 1, characterized by the fact that surfactants that are stable at the prevailing process conditions are used for homogenizing the reaction mixture.

10. Process according to claim 9, characterized by the fact that a surfactant known for the preparation of perfluorocarbons is used as the surfactant.

11. Process according to claim 1, characterized by the fact that surfactants from the group of fluorosurfactants that are stable in strongly alkaline media of the type $R_FCOOH$ or $R_FSO_3H$ ($R_F=CF_3(CF_2)_n$, $n=3-10$) or their anions, $R_FCOO^-$ or $R_FSO_3^-$, are used.

12. Process according to claim 11, characterized by the fact that the surfactants are used in concentrations of 0.05–0.5, maximally 1.0 wt %.

13. Process according to claim 1, characterized by the fact that after completion of the entire purification process, the surfactant-containing aqueous alkaline phase is reused.

14. Process according to claim 1, characterized by the fact that the perfluorocarbons to be purified are reacted with the reactants in a "single-batch" process.

* * * * *